US00PP27618P2

(12) United States Plant Patent
Hansen

(10) Patent No.: US PP27,618 P2
(45) Date of Patent: Jan. 24, 2017

(54) ***MONARDA* PLANT NAMED 'CHERRY POPS'**

(50) Latin Name: ***Monarda didyma* L.**
Varietal Denomination: Cherry Pops

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/545,873

(22) Filed: Jun. 30, 2015

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct plant cultivar of ornamental bee balm named *Monarda didyma* 'Cherry Pops' has rapid-growing, short, compact, branching stems, dark green foliage, numerous cherry red flowers on dark purplish tinted stems. Foliage has good resistance to powdery mildew.

1 Drawing Sheet

FEDERAL SPONSORSHIP AND FUNDING

This plant invention was developed without federally sponsored research or development funding.

BOTANICAL DESIGNATION AND CULTIVAR DENOMINATION

Botanical classification: *Monarda didyma* L.
Variety denomination: 'Cherry Pops'.

BACKGROUND OF THE INVENTION

The present invention relates to the new and distinct cultivar botanically known as *Monarda didyma* 'Cherry Pops', and hereinafter also referred to solely as the cultivar 'Cherry Pops' or the "new plant". The new plant was the subject of an open pollination in summer of 2010 at a wholesale perennial nursery in Zeeland, Mich., USA. Seed was harvested by the inventor in the fall of 2010 and later the individual seedling later assigned the breeder identification number H10-09-51. The female or seed parent is the unreleased proprietary hybrid *Monarda didyma* HK9-44-40 (not patented) and the male or pollen parent is unknown but may have been any one of a number of plants and seedlings in the breeding area since the pollen is efficiently spread long distances by insects. The plant was initially subjected to evaluation in the summer of 2011 in trial plots of the same nursery in Zeeland, Mich. The new plant was collected and set apart as a single selected seedling in July of 2012 and separated out for final evaluation in the summer of 2013 by Hans Hansen.

The plant has been asexually propagated by stem cuttings as early as the summer of 2012 at the same nursery in the greenhouses in Zeeland, Mich., and the subsequent asexually propagated plants found to be stable and identical to the original selection.

BRIEF SUMMARY OF THE PLANT

*Monarda didyma* 'Cherry Pops' is unique from its parent and all other bee balm plants known to the inventor. The nearest comparison varieties are 'Fireball' U.S. Plant Pat. No. 14,235 and 'AChall' (U.S. Plant Pat. No. 19,582) in plant habit 'Jacob Cline' (not patented), 'Colrain Red' (not patented), 'Fire Marshall' U.S. Plant Pat. No. 23,286, 'Fireball' U.S. Plant Pat. No. 14,235, 'Mondid 0803' U.S. Plant Pat. No. 17,513, 'Cambridge Scarlet' (not patented) and 'Gardenview Scarlet' (not patented) along with 'Fireball' and 'AChall' all have a reddish based flower color. Compared to 'Cherry Pops' all of the above have more purplish tinting or deeper red in flower color than 'Cherry Pops' which has a lighter cherry red flower color. Compared to the parent, the new plant is shorter and has more cherry red flower color.

The table below shows a more detailed comparison of these cultivars in terms of flower color and height.

TABLE 1

| MONARDA CULTIVAR | FLOWER COLOR | HEIGHT |
|---|---|---|
| 'Achall' | red-purple | 46 cm |
| 'Cambridge Scarlet' | scarlet | 84 cm |
| 'Cherry Pops' | cherry red | 50 cm |
| 'Colrain Red' | deep red | 122 cm |
| 'Fire Marshall' | deep red | 50 cm |
| 'Fireball' | ruby red | 60 cm |
| 'Gardenview Scarlet' | scarlet | 84 cm |
| 'Jacob Cline' | red-purple | 92 cm |
| 'Mondid 0803' | red-purple | 40 cm |

The following are traits of *Monarda didyma* 'Cherry Pops' that in combination distinguish it from all other bee balm plants known to the inventor:

1. Rapid-growing, intermediate height, compact, tightly clumping habit.
2. Dark-green, powdery mildew resistant foliage.
3. Dark purplish tinted stems.
4. Cherry red flowers for a long period in summer.

BRIEF DESCRIPTION OF THE DRAWINGS

The photographs of the new plant demonstrate the unique traits of 'Cherry Pops' and the overall appearance of the plant at three-years-old in the full sun trial garden of a nursery in Zeeland, Mich. The colors are as accurate as reasonably possible with current color reproduction technology. Deviation in ambient light spectrum, source and direction may cause the appearance of minor variation in color.

DETAILED BOTANICAL DESCRIPTION

Figure 1:
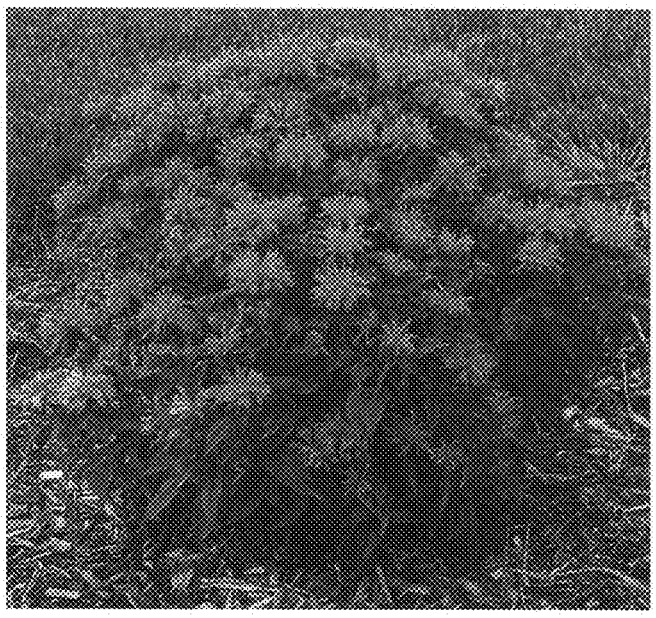
FIG. 1 shows the new plant in flower.
Figure 2:
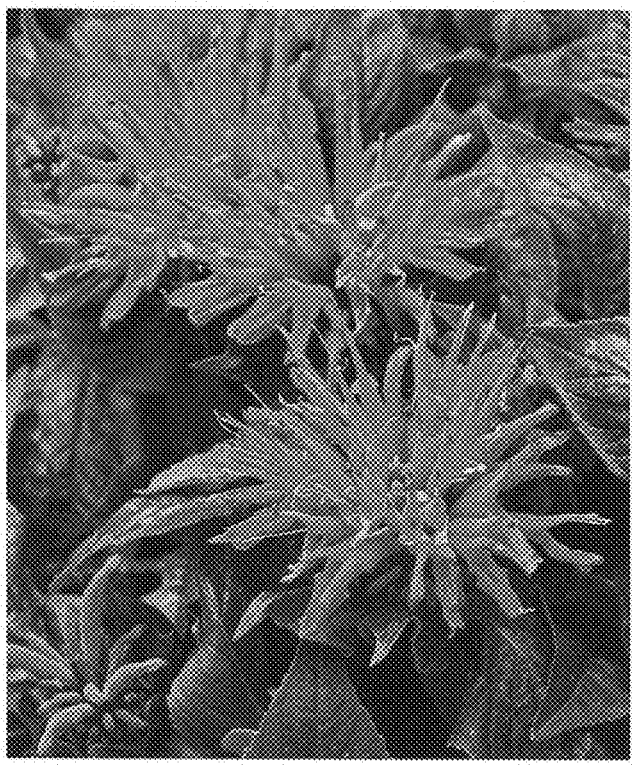
FIG. 2 shows a close-up of the flowers.

The following descriptions and color references are based on the 2001 edition of The Royal Horticultural Society Colour Chart except where common dictionary terms are used. *Monarda didyma* 'Cherry Pops' has not been observed under all possible environments. The phenotype may vary slightly with different growing environments such as temperature, light, fertility, soil pH, moisture and maturity levels, but without any change in the genotype. The following observations and size descriptions axe based on two-year old garden-grown plants in full sun at a nursery in Zeeland, Mich. with minimal supplemental fertilizer and water as needed but without plant growth regulators or pinching.

Botanical classification: *Monarda didyma.*

Parentage: Female (seed) parent is *Monarda didyma* HK9-44-40 (not patented); male (pollen) parent is unknown.

Plant habit: Hardy, herbaceous, compact perennial, producing several stems, spreading by short rhizomes; 38 to 50 cm tall at flowering and about 72 cm wide; flowering begins mid-summer in Michigan and continues for about 5 to 7 weeks.

Propagation: Stem cuttings.

Time to produce finished crop in 3.8 liter pots: About 7 to 9 weeks; moderately fast rate of growth.

Root: Fine, fibrous and freely branching; color creamy white to tan depending on soil type.

Leaves: Simple, lanceolate, opposite, serrated, slightly puberulent above and puberulent below; surfaces lustrous above, matte below; acute apex, ovate to rounded base; average about 6.8 cm long by about 3.0 cm. wide.

Leaf color: Young leaves between RHS 137D and RHS 146C above and between RHS 146B and RHS 138B below; older leaves nearest RHS 136A above with tinting of nearest RHS 187B with more direct sunlight and nearest RHS 138C below.

Foliage fragrance: Pleasantly lemony.

Veins: Pinnate; pubescent below with minutely puberulent above, slightly sunken above and raised below.

Vein color: Adaxial midrib nearest RHS 136A, center portion of lateral veins nearest RHS 135A above with distal vein portion nearest RHS 136A; abaxial midrib and center portion of lateral veins between RHS 157D and RHS 145D with distal portion of lateral veins between RHS 136D and RHS 137D.

Petiole: Pubescent, slightly concaved above; average about 10.0 mm long and 2.0 mm across.

Petiole color: Between RHS 144D and RHS N144D above and below with slight tinting of nearest RHS N186C where exposed to intense direct sunlight.

Stems: Squared, puberulent, densely pubescent at nodes; 4.0 to 7.0 mm across at base, average about 5.0 mm across.

Nodes: 8 to 10 per stem; average internode length about 4.0 cm, closer at base; node color same as surrounding stem.

Stem color: Nearest RHS 145C with tinting of nearest RHS 187B becoming more concentrated in upper portion, central portion between RHS 145C and RHS N144D generally without purplish gray tinting and base portion more purple than RHS N186C and more grayed than RHS 79C.

Flowers: Single labiate flowers arranged in terminal globular head about 6.8 cm across and 3.8 cm tall opening from the center and progressing outwardly and down; individually persisting about 5 days in Michigan; numerous, about 200 flowers per head; self-cleaning.

Flower fragrance: Moderately spicy.

Buds one to two days prior to opening: Narrowly oblanceolate, distinctly curved downward; about 2.3 cm long and 3.0 mm diameter.

Bud color one to two days prior to opening: Between RHS 61B and RHS 62C in distal one third with a lighter base of white, lighter than RHS N155D or RHS 155D.

Petals: Labiate; lower curved downward and upper nearly straight; split in two in the distal 1.3 cm with upper lip fused into a hood about 3.4 cm long and 2.5 mm diameter; lower lip about 3.6 cm long comprising three lobes including two side lobes about 1.0 mm long with rounded apex and center lobe about 4.0 to 5.0 mm long split in the distal 1.0 mm with acute apex, curled up and back underneath almost 270 degrees; both side lobes glandular and pubescent outer surfaces with fine hairs the same color as petals; both lobes glabrous on inner surfaces.

Petal color: Color of all petals on both surfaces between RHS 58B and RHS 58C with basal 5.0 mm white, lighter than RHS 155D or RHS N155D.

Filaments: Two, about 3.2 cm long by about 0.8 mm diameter across at the widest point.

Filament color: Lighter than RHS N155D in the middle portion and below developing distal tinting of nearest RHS 61B.

Anther: Oblong elliptic, dorsifixed, longitudinal; about 2.8 mm long by about 1.0 mm across.

Anther color: Between RHS 44B and RHS 44C along dehiscence marginal line and nearest RHS 187A and lighter than RHS 23D in the center at point of attachment to filament.

Pollen: Abundant, elliptic to globose, less than 0.1 mm; color nearest RHS 15D.

Pistil: One per flower.

Style: About 3.9 cm long by about 0.25 mm diameter; color nearest RHS N155C with tinting increasing at distal end to nearest RHS 61B.

Stigma: Split in two in the distal 2.0 mm, less than 0.25 mm in diameter, color nearest RHS 64A.

Ovary: 1.0 mm by 0.75 mm, between RHS 143D and RHS 144B.

Sepals: Five, entire, apiculate apex, base fused forming corolla about 9.0 mm long split in about the apical 2.0 mm, about 2.0 mm diameter at base and about 3.0 mm diameter at distal end; apex glandular and with minute hairs on outer surface, glabrous on inner surface.

Sepal color: While still in young bud base nearest RHS 186C with apical margin and corolla fusion lines between RHS 186A and RHS N186D; after flower abscission apical margin and corolla fusion lines nearest RHS 187A with portions between and inner surface between RHS 187 B and RHS 187C.

Peduncle: Pubescent, stiff, strong, branched, erect, squared to about 0.7 cm across at base and 38 cm long; about 45 per plant.

Peduncle color: Nearest RHS 145C with tinting of nearest RHS 187B becoming more concentrated in upper portion.

Bracts: Five to nine subtending flower head; acute apex with base sessile and truncate; size decreasing distally, to about 1.5 cm long and 1.2 cm wide at base.

Bract color: Lowest bracts same color as leaves; distally becoming more pigmented to between solid RHS 187A and RHS N187A in both abaxial and adaxial surfaces; intermediate bracts between RHS 187A and RHS N187A toward apex and between RHS 146A and RHS 147A toward middle of both abaxial and adaxial surfaces with veining nearest RHS 61B both surfaces.

Fruit: Single nutlet, elliptical, about 1.0 mm long and 0.7 mm wide; color nearest RHS 202A.

Hardiness: The new plant grows best with plenty of moisture and adequate drainage; hardy from at least from USDA zone 4 through 8.

Disease and pest resistance: Demonstrated powdery mildew resistance in side by side comparison at least equal that of 'ACrade' and better than 'AChall' and 'Pink Lace' U.S. Plant Pat. No. 18,367.

I claim:

1. A new and distinct plant cultivar *Monarda didyma* 'Cherry Pops', as herein described and illustrated, resistant to powdery mildew and suitable for the garden landscape, or as a potted plant, patio, and for cut flower arrangements.

* * * * *